United States Patent [19]

Thiele

[11] 4,215,144

[45] * Jul. 29, 1980

[54] METHOD OF TREATING AND CONTROLLING GINGIVITIS

[75] Inventor: Geraldine H. Thiele, New Oxford, Pa.

[73] Assignee: Oxford Hill Ltd., New Oxford, Pa.

[ * ] Notice: The portion of the term of this patent subsequent to Jun. 27, 1995, has been disclaimed.

[21] Appl. No.: 918,817

[22] Filed: Jun. 26, 1978

[63] Continuation of Ser. No. 755,400, Dec. 29, 1976, Pat. No. 4,097,054, which is a continuation-in-part of Ser. No. 890,239, Mar. 27, 1978, which is a continuation of Ser. No. 642,114, Dec. 18, 1975, which is a continuation-in-part of Ser. No. 724,942, Sep. 20, 1976, which is a continuation-in-part of Ser. No. 724,943, Sep. 20, 1976, which is a continuation-in-part of Ser. No. 113,362, Feb. 8, 1971, Pat. No. 3,741,204, which is a continuation-in-part of Ser. No. 123,830, Mar. 12, 1971, Pat. No. 3,767,812, which is a continuation-in-part of Ser. No. 283,662, Aug. 25, 1972, Pat. No. 3,805,776, which is a continuation-in-part of Ser. No. 283,663, Aug. 25, 1972, Pat. No. 3,828,772, which is a continuation-in-part of Ser. No. 369,236, Jun. 12, 1973, Pat. No. 3,924,000, and a continuation-in-part Ser. No. 483,010, Jun. 25, 1974, Pat. No. 3,982,017, said Ser. No. 890,239, is a continuation of said Ser. No. 724,943, which is a continuation of said Ser. No. 483,010, which is a continuation-in-part of Ser. No. said 369,236, which is a continuation-in-part of said Ser. No. 283,663, which is a continuation-in-part of said Ser. No. 283,662, which is a continuation-in-part of said Ser. No. 123,830, and a continuation-in-part of Ser. No. 113,362, said Ser. No. 755,400 is a continuation of said Ser. No. 642,114, which is a continuation-in-part of said Ser. No. 483,010, which is a continuation-in-part of said Ser. No. 369,236, which is a continuation-in-part of said Ser. No. 283,663, which is a continuation-in-part of said Ser. No. 283,662, which is a continuation-in-part of said Ser. No. 123,830, and a continuation-in-part of Ser. No. 113,362, said Ser. No. 724,943 which is a continuation-in-part of said Ser. No. 483,010, which is a continuation-in-part of said Ser. No. 369,236, which is a continuation-in-part of said Ser. No. 283,663, which is a continuation-in-part of said Ser. No. 283,662, which is a continuation-in-part of said Ser. No. 123,830, and a continuation-in-part of said Ser. No. 113,362, said Ser. No. 724,942 is a continuation-in-part of said Ser. No. 483,010, which is a continuation-in-part of said Ser. No. 369,236, which is a continuation-in-part of said Ser. No. 283,663, which is a continuation-in-part of said Ser. No. 283,662, which is a continuation-in-part of said Ser. No. 123,830, and a continuation-in-part of said Ser. No. 113,362, said Ser. No. 642,112, which is a continuation-in-part of said Ser. No. 483,010, which is a continuation-in-part of said Ser. No.369,236, which is a continuation-in-part of said Ser. No. 283,663, which is a continuation-in-part of said Ser. No. 283,662, which is a continuation-in-part of said Ser. No. 123,830, which is a continuation-in-part of said Ser. No. 113,362, said Ser. No. 483,010 is a continuation-in-part of said Ser. No. 369,236, which is a continuation-in-part of said Ser. No. 283,663, which is a continuation-in-part of said Ser. No. 283,662, which is a continuation-in-part of said Ser. No. 123,830, and a continuation-in-part of said Ser. No. 113,362, said Ser. No. 369,236 which is a continuation-in-part of said Ser. No. 283,663, which is a continuation-in-part of said Ser. No. 283,662, which is a continuation-in-part of said Ser. No. 123,830 and a continuation-in-part of said Ser. No. 113,362 said Ser. No. 283,663 is a continuation-in-part of said Ser. No. 123,830 and a continuation-in-part of said Ser. No. 113,362, said Ser. No. 283,662 is a continuation-in-part of said Ser. No. 123,830 and a continuation-in-part of said Ser. No. 113,362, said Ser. No. 123,830 is a continuation-in-part of said Ser. No. 113,362.

[51] Int. Cl.$^2$ .......................... A61K 31/20; A61K 31/45
[52] U.S. Cl. ........................................ 424/318; 424/343
[58] Field of Search ................................ 424/318, 343

[56] References Cited

OTHER PUBLICATIONS

Prinz—Dental Formulary–3rd Ed. p. 145 (1923).
Accepted Dental Therapeutics–35th Ed. p. 308 (1973).
Chem. Abst. 63 955(e) (1965)–Vellati et al.
Chem. Abst. 15 1164$^4$ (1921)–Davis et al.
Chem Abst. 20 1457$^5$ (1926).
J. Bact. 44 pg. 6570$^6$ (1942) Dred Primary Examiner—Douglas W. Robinson
Attorney, Agent, or Firm—Fisher, Christen & Sabol

[57] ABSTRACT

The method of treating and controlling gingivitis and related periodontal diseases of the gingival tissue. The method includes contacting the diseased gingival tissue with a mouthwash. The mouthwash is a liquefied composition of 0.5 to 10 percent by weight of a fatty salt prepared from an unsubstituted, unsaturated fatty acid having at least one double bond and from an alkali metal or an alkali metal compound or an alkali metal basic compound, a liquid carrier, an effective amount of a buffering agent and an effective amount of ethanol. The pH of the liquefied composition is between 8 and 11. The preferred mouthwash contains about 5 percent of sodium oleate, about 1.5 percent of ethanol, enough disodium hydrogen phosphate to adjust the pH to about 9.8 and the remainder water.

2 Claims, No Drawings

METHOD OF TREATING AND CONTROLLING GINGIVITIS

This application is a continuation of application Ser. No. 755,400, entitled "Mouthwash and Method For Preventing and Removing Dental Plaque", which was filed on Dec. 29, 1976, now U.S. Pat. No. 4,097,064, is a continuation-in-part of application Ser. No. 890,239, entitled "Injectable Solutions and Processes of Using Such", which was filed on Mar. 27, 1978, is a continuation of application Ser. No. 642,114, entitled "Mouthwash and Method for Preventing and Removing Dental Plaque", which was filed on Dec. 18, 1975, is a continuation-in-part of application Ser. No. 724,942, entitled "Mouthwash and Method For Preventing and Removing Dental Plaque", which was filed on Sept. 20, 1976, is a continuation-in-part of application Ser. No. 724,943, entitled "Injectable Solutions and Processes of Using Such", which was filed on Sept. 20, 1976, is a continuation-in-part of application Ser. No. 113,362, entitled "Method of Treating Bone Fractures and Non-Unions", which was filed on Feb. 8, 1971, now U.S. Pat. No. 3,741,204, is a continuation-in-part of application Ser. No. 123,830, entitled "Non-Surgical Removal of Abnormal New Bone Proliferation", which was filed on Mar. 12, 1971, now U.S. Pat. No. 3,767,812, is a continuation-in-part of application Ser. No. 283,662, entitled "Treatment of Non-Surgical Osteolysis of Bone", which was filed on Aug. 25, 1972, U.S. Pat. No. 3,805,776, is a continuation-in-part of application Ser. No. 283,663, entitled "Method of Fusing Bones", which was filed on Aug. 25, 1972, now U.S. Pat. No. 3,828,772, is a continuation-in-part of application Ser. No. 369,236, entitled "Injectable Solution", which was filed on June 12, 1973, now U.S. Pat. No. 3,924,000; and is a continuation-in-part of application Ser. No. 483,010, entitled "Injectable Solutions and Processes of Using Such", which was filed on June 25, 1974, now U.S. Pat. No. 3,982,017; application Ser. No. 890,239, is a continuation of application Ser. No. 724,943, is a continuation of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 755,400 is a continuation of application Ser. No. 642,114, is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 724,943 is a continuation of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 724,942 is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 642,112 is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 483,010 is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 369,236 is a continuation-in-part of application Ser. No. 283,663, is a continuation-in-part of application Ser. No. 283,662, is a continuation-in-part of application Ser. No. 123,830 and is a continuation-in-part of application Ser. No. 113,362; application Ser. No. 283,663 is a continuation-in-part of application Ser. No. 123,830 and is a continuation-in-part of application Ser. No. 113,362; application Ser. No. 283,662 is a continuation-in-part of application Ser. No. 123,830 and is a continuation-in-part of application Ser. No. 113,362; and application Ser. No. 123,830 is a continuation-in-part of application Ser. No. 113,362.

FIELD OF THIS INVENTION

This invention relates to the prevention and removal of dental plaque.

BROAD DESCRIPTION OF THIS INVENTION

An object of this invention is to provide a process for the prevention and removal of dental plaque and dental calculus, and the prevention of dental caries. Other objects and advantages of this invention are set out elsewhere herein or are obvious to one ordinarily skilled in the art herefrom.

This invention achieves the objects and advantages of this invention.

This invention involves a method of treating teeth for the removal of dental plaque and/or dental calculus from teeth and the prevention of the formulation of dental plaque and/or dental calculus on teeth. The process involves contacting the teeth with a sufficient and effective amount to achieve such purpose of a mouthwash. The mouthwash is a liquefied composition of an effective amount of a non-necrotic fatty acid compound prepared from an unsubstituted, unsaturated fatty acid having at least one double bond, a liquid carrier, an effective amount of a buffering agent and an effective amount of ethanol, the pH of said liquefied composition being between 8 and 11.

The most preferred mouthwash contains about 5 percent of sodium oleate, about 1.5 percent of ethanol, enough disodium hydrogen phosphate to adjust the pH to about 9.8, and the remainder water.

This invention also includes the method of treating teeth for the prevention of caries or tooth decay. The method includes contacting the teeth with a sufficient and effective amount to achieve the purpose of a mouthwash. The mouthwash is a liquefied composition of an effective amount of a non-necrotic fatty acid compound prepared from an unsubstituted unsaturated fatty acid having at least one double bond, a liquid carrier, an effective amount of a buffering agent and an effective amount of ethanol, the pH of said liquefied composition being between 8 and 11. The most preferred mouthwash contains about 5 percent of sodium oleate about 1.5 percent of ethanol, enough disodium hydrogen phosphate to adjust the pH to about 9.8 and the remainder water.

This invention further includes the mouthwash composition which is a liquefied composition comprised of an effective amount of a non-necrotic fatty acid compound prepared from an unsubstituted, unsaturated fatty acid having at least one double bond, a liquid carrier, an effective amount of a buffering agent and an effective amount of ethanol. The pH of said liquefied composition is between 8 and 11. The most preferred mouthwash composition contains about 5 percent of sodium oleate, about 1.5 percent of ethanol, enough disodium hydrogen phosphate to adjust the pH to about 9.8 and the remainder water.

An important advantage of this invention is that no abrasive material, like that used in most toothpastes and dentifices, has to be used in order to remove and prevent dental plaque formation. A further advantage of this invention is that the mouthwash of this invention eliminates the need to have dentists remove dental plaque from teeth by scrapping with sharpened tools or instruments.

The mouthwash is particularily effective in preventing cavities or caries around metal teeth braces. (Any mouthwash containing HCl or other acid would react with metal teeth braces.)

The mouthwash also substantially alleviates the sensitivity syndrome of teeth.

DETAILED DESCRIPTION OF THIS INVENTION

The term liquefied composition includes slurries, suspensions, solutions, etc.

All of the components of the liquefied composition must be and are substantially non-toxic in the amounts and under the conditions of use. The useful (vascular sclerosing) fatty acid compounds must be non-necrotic in effect or operation and must not cause the pathologic death of one or more cells, or a portion of any tissue or any organ, resulting from irreversible damage to the nucleus.

The pH of the liquefied composition should be between about 8 and about 11, and preferably between about 9 and about 10. Each non-necrotic (sclerosing) unsaturated fatty acid compound will produce a different pH at a different concentration levels, so non-toxic agents may be added to adjust the pH level, e.g., sodium dihydrogen phosphate or sodium hydroxide can be used when sodium oleate or another non-necrotic (vascular sclerosing) unsaturated fatty acid compound is used.

It should be noted that aqueous solutions of alkali metal salts of fatty acids in general have an alkaline or neutral pH. For example, sodium oleate has an alkaline pH—this is usually due to hydrolysis in the aqueous solution.

The most preferred unsaturated fatty acids have eighteen carbon atoms with one double bond in the middle of the chain. The most preferred of such fatty acids is oleic acid (i.e., cis-9-oleic acid or cis-9-octadecenoic acid). The next preferred of such fatty acids is elaidic acid (i.e., trans-9-octadecenoic acid).

Examples of other unsaturated fatty acids having one double bond (i.e., monoethenoid fatty acids) having eighteen carbon atoms are: 2-octadecenoic acid (cis and trans forms), $CH_3(CH_2)_{14}CH=CHCOOH$-3-octadecenoic acid, $CH_3(CH_2)_{13}CH=CHCH_2COOH$; 4-octadecenoic acid, $CH_3(CH_2)_{12}CH=CH(CH_2)_2COOH$; 5-octadecenoic acid, $CH_3(CH_2)_{11}CH=CH(CH_2)_3COOH$; 6-octadecenoic acid (cis and trans forms), $CH_3(CH_2)_{10}CH=CH(CH_2)_4COOH$; 7-octadecenoic acid (cis and trans forms), $CH_3(CH_2)_9CH=CH(CH_2)_5COOH$; 8-octadecenoic acid (cis and trans forms; 10-octadecenoic acid, (cis and trans form), $CH_3(CH_2)_6CH=CH(CH_2)_8COOH$; 11-octadecenoic acid (cis and trans form), $CH_3(CH_2)_5CH=CH(CH_2)_9COOH$; 12-octadecenoic acid (cis and trans form), $CH_3(CH_2)_4CH=CH(CH_2)_{10}COOH$; 15-octadecenoic acid (trans form), $CH_3CH_2CH=CH(CH_2)_{13}COOH$; 16-octadecenoic acid (trans form), $CH_3CH=CH(CH_2)_{13}CH_2COOH$; and 17-octadecenoic acid $CH_2=CH(CH_2)_{14}CH_2COOH$ (It is believed that the fatty acids having the unsaturation at one end of the hydrocarbon chain, or not in the center thereof, have some undesirable properties and effects in the processes of this invention, e.g., less complete and slower dental plaque removal and prevention—such compounds are useful, but are certainly much less preferred in result.)

Examples of other useful monaethenoid fatty acids are: 2-tridecenoic acid; 11-tridecenoic acid; 12-tridecenoic acid; 2-dodecenoic acid; 5-dodecenoic acid; 6-dodecenoic acid; 7-dodecenoic acid; 9-dodecenoic acid; 10-dodecenoic acid; 11-dodecenoic acid; 9-eicosenoic acid, $CH_3(CH_2)_9CH=CH(CH_2)_7COOH$; 11-eicosenoic acid; 14-eicosenoic acid; 2-undecenoic acid; 6-undecenoic acid; 9-undecenoic acid; 10-undecenoic acid; 2-decenoic acid; 3-decenoic acid; 4-decenoic acid; 8-decenoic acid; 9-decenoic acid; acrylic acid, $CH_2=CHCOOH$; β-methylacrylic acid (cis and trans forms), $CH_3CH=CHCOOH$; α-methylacrylic acid, $CH_2=C(CH_3)COOH$; vinyl acetic acid, $CH_2=CHCH_2COOH$; β,β-dimethylacrylic acid, $(CH_3)_2C=CHCOOH$; β-pentenoic acid, $CH_3CH=CHCH_2COOH$; allylacetic acid, $CH_2=CHCH_2CH_2COOH$; angelic acid, $CH_3CH=C(CH_3)COOH$ (cis form); tiglic acid, $CH_3CH=C(CH_3)COOH$ (trans form); 2-heptadecenoic acid, $CH_3(CH_2)_{12}CH_2CH=CHCOOH$; 9-heptadecenoic acid (cis and trans forms), $CH_3(CH_2)_6CH=CH(CH_2)_7COOH$ 2-hexadecenoic acid, $CH_3(CH_2)_{12}CH=CHCOOH$; 9-hexadecenoic acid (cis form); 2-tetradecenoic acid; 4-tetradecenoic acid; 5-tetradecenoic acid; 8-tetradecenoic acid; 9-tetradecenoic acid; 2-nonenoic acid; 3-nonenoic acid; 8-nonenoic acid; 2-octenoic acid; 3-octenoic acid; 7-octenoic acid; 2-heptenoic acid; 3-heptenoic acid; 4-heptenoic acid; 5-heptenoic acid; 6-heptenoic acid; 2-hexenoic acid; 3-hexenoic acid; 4-hexenoic acid; 5-hexenoic acid; 15-tetracosenoic acid; 17-hexacosenic acid; and 21-triacentenoic acid.

Examples of fatty acids having a triple bond are: 2-nonynoic acid, $CH_3(CH_2)_5C\equiv CCOOH$; 3-nonynoic acid; 4-nonynoic acid; 5-nonynoic acid; 6-nonynoic acid; 7-nonynoic acid; and 8-nonynoic acid.

Examples of diethenoid fatty acids having eighteen carbon atoms are: 6:8-octadecadienoic acid, $CH_3(CH_2)_8CH=CHCH=CH(CH_2)_4COOH$ 8:10-octadecadienoic acid, (8-trans and 10-trans forms); 8:11-octadecadienoic acid, (8-cis and 11-cis forms); 9:11-octadecadienoic acid, (9-cis and 11-cis and 11-trans forms); 5:12-octadecadienoic acid, (5-cis, 5-trans, 12-trans and 12-cis forms); 9:12-octadecadienoic acid, (9-cis, 9-trans, 12-trans and 12-cis forms); 10:12-octadecadienoic acid, (10-cis, 10-trans, 12-cis and 12-trans forms); 10:13-octadecadienoic acid, (10-cis and 13-cis forms); and 11:14-octadecadienoic acid, (11-cis and 14-cis forms).

Examples of other useful diethenoid acids are β-vinylacrylic acid CH$_2$=CHCH=CHCOOH; sorbic acid, CH$_3$CH=CHCH=CHCOOH; and geranic acid, (CH$_3$)$_2$C=CH(CH$_2$)$_2$C(CH$_3$)=CHCOOH.

Examples of tetra and triethenoid fatty acid having eighteen carbon atoms are: 9:11:13:15-octadecatetraenoic acid, CH$_3$CH$_2$(CH$_2$=CH$_2$)$_4$(CH$_2$)$_7$COOH; 6:9:12:15-octadecatetraenoic acid; 5:9:12-octadecatrienoic acid (5-trans, 9-cis and 12cis forms); CH$_3$(CH$_2$)$_4$CH=CHCH$_2$CH=CH(CH$_2$)$_2$CH=CH(CH$_2$)$_3$COOH; 6:9:12-octadecatrienoic acid; 6:10:14-octadecatrienoic acid; 8:10:12-octadecatrienoic acid (8-cis, 10-trans and 12 cis forms), 9:11:13-octadecatrienoic acid (9-cis, 11-trans and 13 trans forms); 9:12:15-octadecatrienoic acid (9-cis, 9-trans, 12-cis, 12-trans, 15-cis and 15-trans forms; and 10:12:14-octadecatrienoic acid (10-trans, 12-trans and 14-trans forms).

An example of a useful triethenoid fatty acid is dehydrogeranic acid, (CH$_3$)$_2$C=CHCH=CHC(CH$_3$)=CHCOOH.

Examples of fatty acids having four double bonds are clupandoic acid, moroctic acid, arachidonic acid, α-parinaric acid, and β-parinaric acid.

The useful unsaturated fatty acids can contains between 1 and 50 carbon atoms, preferably between 14 and 22 carbon atoms and most preferably by a wide margin have 18 carbon atoms.

Examples of useful unsaturated fatty acids are oleic acid, licanic acid, eleostearic acid and clupanodonic acid. The useful unsaturated fatty acids can be those containing one double bond, e.g., oleic acid, two double bonds, e.g, linoleic acid, three double bonds, e.g., eleostearic acid, etc.

Within the scope of this invention, saturated fatty acid compounds are not useful. The mechanism requires fatty acid moiety unsaturation. Compositions containing mixtures of saturated and unsaturated fatty acid compounds, e.g., sodium morrhuate, should not be used due to the presence of any substantial amount of saturated fatty acid compounds. Sodium morrhuate is a mixture of the sodium salts of unsaturated and saturated fatty acids of cod liver oil.

Fatty acids which contain one or more hydroxyl groups (not containing the acid portion), e.g., dihydroxystearic acid and ricinoleic acid, are not useful within the scope of this invention. For example, the negative hydroxyl group in ricinoleic acid does not produce the necessary (cell) differentiation—this applies to all negative substituents on the main carbon chain. A high ammonia content will erode and "eat" the tooth enamel. These factors, plus degree of effectiveness, etc., are why the fatty acid compound should not be a substituted one. The fatty acid must not by cyclic. The fatty acid is probably not branch chained. The fatty acid should be straight chained, with unsaturation at the center of the carbon chain.

The fatty acid compounds can be soaps such as the reaction product of fatty acids and organic bases—but such are not preferred compounds. The fatty acid compounds can be esterified fatty acids. The fatty acid compound are most preferably a fatty acid salt. The fatty acid salts can be those prepared from metals such as, aluminum and alkaline earth metals, e.g., calcium, but are preferably those prepared by alkali metals, e.g., sodium (preferred), lithium, potassium, caesium and rubidium. (Ionic fatty acid compounds of sodium, such as, sodium oleate, are preferred even though the potassium salts are usually more soluble. Also, when the sodium balance becomes a factor, the sodium salts are the most preferred.) The metals are used as hydroxides, carbonates, etc. The fatty acid salts can be prepared from non-metallic inorganic bases, but such is not a preferred category of compounds. By way of summary for the alkali metals, the fatty acid salt can be prepared from an unsubstituted unsaturated fatty acid having one double bond and from an alkali metal or an alkali metal compound or a basic alkali metal compound.

The most preferred compound is sodium oleate.

Examples of useful compounds of oleic acid are: the methyl ester of cis-9-octadecenoic acid; ethyl ester of cis-9-octadecenoic acid; propyl ester of cis-9-octadecenoic acid; isopropyl ester of cis-91 -octadecenoic acid; butyl ester of cis-9-octadecenoic acid; isobutyl ester of cis-9-octadecenoic acid; tert.-butyl ester of cis-9-octadecenoic acid; 3-methylbutyl ester of cis-9-octadecenoic acid; 2-methyl-2-butyl ester of cis-9-octadecenoic acid; phenyl ester of cis-9-octadecenoic acid; m-tolyl ester of cis-9-octadecenoic acid; p-phenylphenacyl ester of cis-9-octadecenoic acid; and the amide ester of cis-9-octadecenoic acid.

Examples of useful compounds of elaidic acid are: the methyl ester of trans-9-octadecenoic acid; the ethyl ester of trans-9-octadecenoic acid; and the amide ester of trans-9-octadecenoic acid.

Examples of useful octadecenoic acid compounds are: the methyl ester of trans-2-octadecenoic acid; the ethyl ester of trans-2-octadecenoic acid; the amide ester of trans-2-octadecenoic acid; the methyl ester of trans-3-octadecenoic acid; the methyl ester of cis-6-octadecenoic acid; the p-bromophenacyl ester of cis-6-octadecenoic acid; the amide of cis-6-octadecenoic acid; the triglyceride of cis-6-octadecenoic acid; the ethyl ester of trans-10-octadecenoic acid; the amide ester of trans-10-octadecenoic acid; the p-bromophenacyl ester of cis-11-octadecenoic acid; the methyl ester of trans-11-octadecenoic acid; the ethyl ester of cis-12-octadecenoic acid; and the methyl ester of trans-16-octadecenoic acid.

Examples of other useful monoethenoid fatty acid compounds are: the lithium salt of 9-heptadecenoic acid; the amide of 2-heptadecenoic acid; the methyl ester of 9-heptadecenoic acid; the ethyl ester of 9-heptadecenoic acid; the ethyl ester of 2-hexadecenoic acid; the methyl ester of 9-hexa decenoic acid; the ethyl ester of 9-hexadecenoic acid, the ethyl ester of 2-tetradecenoic acid; the methyl ester of 4-tetradecenoic acid; the ethyl ester of 4-tetradecenoic acid; the methyl ester of 9-tetradecenoic acid; the amide ester of 2-tridecenoic acid; the methyl ester of 12-tridecenoic acid; the ethyl ester of 12-tridecenoic acid; the amide of 7-dodecenoic acid; the ethyl ester of 11-dodecenoic acid; the methyl ester of 11-dodecenoic acid; the amide of 9-eicosenoic acid; the ethyl ester of 9-eicosenoic acid; the methyl ester of 11-eicosenoic acid; the amide of 2-undecenoic acid; the amide of 6-undecenoic acid; the ethyl ester of 9-undecenoic acid; the copper salt of 10-undecenoic acid; the ethyl ester of 10-undecenoic acid; the amide of 10-undecenoic acid; the amide of 2-decenoic acid; the methyl ester of 8-decenoic acid; the ethyl ester of 2-nonenoic acid; the ethyl ester of 8-nonenoic acid; the ethyl ester of 7-octenoic acid; the methyl ester of 7-octenoic acid; the amide of 2-octenoic acid; the methyl ester of 4-heptenoic acid; the methyl ester of 2-hexenoic acid; the ethyl ester of 2-hexenoic acid; the amide of 3-hexenoic acid; the methyl ester of 5-hexenoic acid; the ethyl ester of 2-pentenoic acid; and the amide of 15-tetracosenoic acid.

Examples of useful diethenoid fatty acid compounds having eighteen carbon atoms are: the methyl ester of 6:8-octadecadienoic acid; the methyl ester of 9:11-octadecadienoic acid; the ethyl ester of 9:11-octadecadienoic acid; the sodium salt of 9:12-octadecadienoic acid; the methyl ester of 9:12-octadecadienoic acid; the ethyl ester of 9:12-octadecadienoic acid; the amide of 9:12-octadecadienoic acid; the benzyl amide of 9:12-octadecadienoic acid; and the methyl ester of 10:12-octadecadienoic acid.

Examples of useful triethenoid fatty acid compounds having eighteen carbon atoms are: the methyl ester of 6:10:14-octadecatrienoic acid; the methyl ester of 9:11:13-octadecatrienoic acid; the ethyl ester of 9:11:13-octadecatrienoic acid; the methyl ester of 9:12:15-octadecatrienoic acid; the ethyl ester of 9:12:15-octadecatrienoic acid; and the methyl ester of 10:12:14-octadecatrienoic acid.

Examples of useful triple bond fatty acid compounds are: the methyl ester of 2-nonynoic acid; the methyl ester of 4-nonynoic acid; the methyl ester of 5-nonynoic acid; the methyl ester of 6-nonynoic acid; the methyl ester of 7-nonynoic acid; the methyl ester of 8-nonynoic acid; the amide of 2-nonynoic acid; the amide of 3-nonynoic acid; the amide of 4-nonynoic acid; the amide of 5-nonynoic acid; the methyl ester of 6-nonynoic acid; the amide of 7-nonynoic acid; and the amide of 8-nonynoic acid.

The purity of the unsaturated fatty acid compound is important. A composition containing a high percentage of unsaturated fatty acid moieties will not be very effective and can cause tissue, etc., damage and other problems. The preferred sodium oleate is particularly effective, while quite innoculous in a toxic and necrotic sense.

The liquefied solution should contain between about 0.5 and about 10 percent by weight of the fatty acid compound, and preferably contain between about 1 and about 5 percent by weight of the fatty acid compound.

Examples of the liquid carrier for the non-necrotic fatty acid compounds are water (preferred) monoglycerides, diglycerides, etc. A mixture of water and ethanol is the most preferred liquid carrier; a salt (NaCl) can be added to make an isotonic aqueous solution as the liquid carrier.

The injectable liquefied composition preferably contains a buffering agent, such as, sodium phosphate such as secondary sodium phosphate, sodium carbonate, or the salt of a weak organic acid with a strong base of which sodium citrate is an example. Examples of useful buffers are disodium hydrogen phosphate and sodium dihydrogen phosphate (preferred).

A buffer solution exerts control over large pH changes. The buffer capacity is directly proportional to the concentration of the buffer components. It is desirable to keep a high concentration of buffer components so that the pH does not shift during usage of the mouthwash. To achieve this, the sodium oleate (or the like) should be present in a relatively high concentration so that the buffer components are present in a relatively high concentration.

Ethanol is a solubilizing agent for the sodium oleate, but the ethanol appears to also have a promoting effect, or the like, on the sodium oleate activity. Other solubilizing agents could be used, but the total effectiveness would apparently not be anywhere near as great as when ethanol is used.

Preferably the mouthwash composition is a liquefied composition comprising a sterile aqueous solution containing 1 to 10 percent of sodium oleate, 0.1 to 5 percent of ethanol, enough buffer to adjust the pH to 9 to 10 and the remainder sterile distilled water. Preferably a phosphate buffer is used.

The most preferred mouthwash composition is a liquefied composition comprising a sterile aqueous solution containing 5 percent of sodium oleate, 1.5 percent of ethyl alcohol enough sodium dihydrogen phosphate to adjust the pH to 9.8 and the remainder sterile distilled water.

If desired, in preparing the most preferred composition the pH can be raised to about 10 by the use of sodium hydroxide before the sodium oleate is added. Then the pH is raised back up to 9.8 by the addition of sodium dihydrogen phosphate.

A flavorant or flavorants, in small amounts, can be added. Lemon water can be used a flavorant, but since it is acidic only small amounts should be used so as not to substantially disturb the crucial pH level. While distilled peppermint water can be added as a flavorant can be used, it is preferably not used as it causes too much foam. Any foam-causing agent (outside of the crucial basic ingredients) should be avoided for they tend to keep the mouthwash away from the teeth surfaces. A coloring agent or agents, in small amounts, can be used. A pleasant-odor producing material, can be used. No such additives should be used which hinder the effectiveness of the composition of this invention.

Anodynes in amounts of up to and including about 5 percent by weight may be added. An anodyne is an agent which ahs the power to relieve pain. An example of a useful anodyne is benzyl alcohol.

Suitable preservations can be added in an amount not to exceed 0.5 percent by weight.

Up to about 5 weight percent, based on the weight of the total composition, of mild anesthetics and/or antiseptics can be added. Examples of such materials are chlorobutanol and benzyl alcohol.

In the preferred compositions using sodium oleate, the ethanol and phosphate buffer are pH level are believed to aid and complement the action of the sodium oleate in a slightly synergistic manner (and may provide the key to the extreme effectiveness of the most preferred composition).

The mouthwash of this invention is preferably used by rinsing or gargling with the mouthwash. Each rinsing or gargling should preferably be at least one minute in duration in order to assure removal and prevention of dental plaque. One should rinse or gargle at least once a day with the mouthwash to assure removal and prevention of the dental plaque.

A plaque deposit may be removed by a couple of applications of the mouthwash. The mouthwash appears to remove a portion of the dental plaque with each application, so usually several applications of the mouthwash are needed to remove the plaque. Thereafter, application of the mouthwash helps prevent plaque formation and removes whatever small amount of plaque may have been deposited since the last application (assuming its recent).

The mouthwash of this invention can also be placed (a few drops, for example) on a tooth brush and then used as a liquid dentifrice in order to remove plaque from the teeth. This embodiment is not any where as effective as usage as a mouthwash in removing plaque. This embodiment is most useful in helping preventing further plaque formation, after the plaque has been removed, where one desires to concurrently remove any food particles lodged between the teeth, etc. Even so the mouthwash aspect is best for further plaque formation prevention.

This invention includes any effective method of contacting the mouthwash with the teeth.

The mouthwash can be applied as an aerosal spray using an inert aerosol propellant, e.g., mixture of trichloromonfluoromethane and dichlorodifluoromethane—this is not a very effective method of preventing and removing dental plaque, but could be used. Application can be by means of a simple squeeze bottle (without any aerosol propellant). An important factor is the contacting of all of the teeth surfaces with the mouthwash and rinsing or gargling for a period of time assures such.

The mouthwash of this invention should not be used in a foam or effervescent form. (Sodium fluoride causes an excessive amount of fluoride.)

Fluorides used in dentrifices have delayed the formation of caries but cannot stop their formation. The fluorides, such as, stannous fluoride, fills (pseudo fill in) in the valleys and lesions in the teeth, which help prevent the plaque-causing bacteria, etc., from attaching to the valley surfaces. The fluorides as such do not remove plaque (or prevent plaque formation in other areas of the teeth). The mouthwash composition of this invention prevents the formation of and removes the dental plaque. The use of fluorides causes minute cracks and lesions around fillings. The mouthwash composition of this invention avoids that problem and apparently prevents the formation of such minute cracks and lesions.

Stannous fluoride fills in the cracks in the enamel, but does not strengthen the teeth. The mouthwash of this invention will fill in the enamel cracks with new enamel, thereby strengthening the teeth by as much as five percent or more.

Abramovich and Sabelli, (J. Dent. Res. 53:94, 1974) incubated teeth with streptococcus mutans in vitro after a single topical application of stannous fluoride. They observed spherical bodies on the enamel surface under the scanning electron microscope and protection against enamel damage. They were not certain whether the bodies were plaque remnants or hydroxyapatite and fluoride crystals. If what Abramovich and Sabelli did see was a bonding or esterification of the hydroxyapatite and sodium fluoride crystals, then such an ester could produce a sclerosing (fill in) effect which in fact could produce structural weakness of a tooth. (It has also been reported that fluoride, mostly not in ionic form, has been reported present in human plaque. High concentrations occur after topical application of fluoride and alter the diffusion-limiting properties of the plaque.) If a lesion was not present then this "filling" could act as a detergent to the formation of caries merely by filling in architectural sites and crevices which would otherwise act as containers for thermal genesis and bacterial growth, however, if a lesion (gross or microscopic) was present on the tooth surface, periodontium or around a restoration sight, this "fill in" of hydroxyapatite and fluoride crystals would contribute to structural weakness and possibly to the reduction and/or improper collagen biosynthesis. The void is filled but not by a true union and thereofre a minimum of trauma or torque produced by occlusal stress would tend to break down the ununited fibers around the edges of containment and the lesions would extend or diffuse. (The use of fluoride means that the negative hydroxyl group is present from the hydroxyapatite.)

A discussion of the theory of plaque formation, etc., is helpful as a background for this invention.

The initiation of the caries process is believed to be produced by the interplay of bacteria and a carbohydrate substrate in contact with a susceptible tooth surface. This interaction takes place within the dental plaque which is adherent to the tooth surface.

The first step is the deposition of a soft plaque on the tooth surface. Most of the plaque consists of dead and living bacterial surrounded by a gel-like organic matrix derived from the bacteria and saliva. Inorganic components from saliva and bacteria are also present within the plaque. It has been shown recently that the bacteria in the plaque utilizes sucrose to form extracellular dextran and levan which, together with salivary mucoprotein forms a "biological flue" that cements the bacteria and other particulate matter to the tooth surface.

The plaque appears as a whitish, glistening or dull mat on tooth surfaces. It is not soluble in water and acts as an effective diffusion barrier between the salivary buffers and the tooth surface. After ingesting sucrose, the pH of the plaque drops to about 5 and is maintained at that level for some time. This low pH probably produces the initial decalcification of the tooth surface in the process of caries development.

In the second phase, the plaque undergoes gradual calcification to form dental calculus. It is not known what initiates this calcification process. Bacteria must play a role in some way since conventional animals form much more calculus than their germ-free counterparts. When calcification of plaque occurs, it begins within and between the bacteria. Many foci of calcification begins within the plaque and with time, these foci coalesce.

Dental plaque or bacterial plaque is a mass of filamentous microorganisms and large variety of smaller froms to the surface of a tooth; depending on bacterial activity and environmental factors, can give rise to caries, calculus, or inflammatory chancres in adjacent tissue. *Stedman's Medical Dictionary*, 20th Ed., (1961), p. 1174. Phage is an agent causing destruction or lysis of microorganisms (e.g., bacteria). Plaque is an area cleared by a phage in a bacterial growth; tache vierge. Kenneth, J. H., "A Dictionary of Biological Terms", 8th Ed., D. Van Nostrand Co., Inc., (1963). Dental calculus is (i) tartar or (ii) calcified deposits formed around the teeth. *Stedman's ibid.*, p. 249. Tartar is a brownish or yellow-brown deposit on the teeth, chiefly hydroxyapatite is an organic matrix. *Stedman's, ibid.*, pp. 1483–84.

Dental caries is a localized, progressively destructive disease of the teeth that starts at the external surface (usually the enamel), with the apparent dissolution of the inorganic components by organic acids. These acids are produced in immediate proximity to the tooth by the enzymatic action of masses of microorganisms (in the bacterial plaque) on carbohydrates. The initial demineralization is followed by an enzymatic destruction of the protein matrix. Cavitation and direct bacterial invasion follow. In the dentin, demineralization of the walls of the tubules is followed by bacterial invasion and destruction of the organic matrix. Untreated dental carie progresses to the pulp, resulting in infection and its sequelae. *Stedman's ibid.*, p. 268.

Oleic acid is a bent molecule:

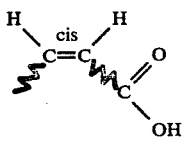

This configuration apparently presents the double bond in a symetric arrangement that has the right amount of reactivity, carbon chain length, double bond position, etc. The configuration of oleic acid and lactobacillic acid hint at the mechanism involved in this mouthwash invention.

The mouthwash of this invention does not disrupt or destroy the normal mouth microflowa, except for the plaque, and does not upset the digestive system (no diarrhea, etc., occurs if the mouthwash is consumed).

Most unsaturated fatty acids are found as the less stable cis isomers rather than the most stable trans isomer. The trans isomers have a double bond that is not in a readily accessable position (the two carbon chain portions protrude in opposite directions), and do not give anywhere as good as results. For this reason, elaidic acid (the trans isomer of the cis isomer, oleic acid) does not give anywhere as good results as does oleic acid.

Fatty acids (cis form) that have two or more double bonds are too reactive to perform in the preferred manner. An example of such is linoleic acid which is too reactive, but is a cis form fatty acid, has two double bonds (somewhat centrally located) and has 18 carbon atoms.

Oleic acid which is $CH_3(CH_2)_7CH=CH(CH_2)_7COOH$, has a melting point of 13° C. Vaccenic acid, which is $Ch_3(CH_2)_5CH=CH(CH_2)_9COOH$, has a melting point of 44° C. This illustrates another reason to have the double bond near the center of the carbon chain-generally such produces a lower melting point, which is important as a liquid fatty acid (salt) is then available over the normal range of usage of the mouthwash.

This invention involves mostly procedures and materials that can be self-administered by the user.

Another embodiment of this invention involves the method of treating and controlling gingivitis and related periodontal diseases of the gingival tissue. The method includes contacting the diseases gingival tissue with a liquefied composition comprised of an effective amount of a non-necrotic fatty acid compound prepared from an unsubstituted, unsaturated fatty acid having at least one double bond, a liquid carrier, an effective amount of a buffering agent and an effective amount of ethanol. The pH of the liquefied composition is between 8 and 11. The mouthwash compositions described herein are useful for this method. The most preferred method is where the said liquefied composition contains about 5 percent of sodium oleate, about 1.5 percent of ethanol, enough disodium hydrogen phosphate to adjust the pH to about 9.8, and the remainder water. This embodiment is particularly useful in treating gingivitis.

This embodiment is useful in preventing and treating of certain peridontal diseases, for example, inflammations of the gums such as, gingivitis and parulis, gingival retraction, receeding of the gum, such as, ulatrophy, etc. Gingivitis is inflammation of the gingival tissues. Types of gingivitis are afunctional gingivitis, gingivitis marginal and cotton-roll gingivitis.

By the treating and alleviating and curing periodontal diseases, such as, gingivitis, with the mouthwash of this invention, loose teeth are tightened with a return to healthy gums. The healthier gums, which have often receded down and away from teeth, frequently return to and near their original positions.

Periodontitis, or pyorrhea, is a disease affecting the supporting tissues of the teeth including the gingiva, the membrane lining the sockets which the teeth lie, and the bones surrounding the teeth. The disease may initially be associated with conditions of constant irritation of the gingiva by dental calculus, food impaction, poor dental restorations, traumatic occlusion, or chemical irritants. So it is seen that this invention can prevent much of the periodontitis.

The gums may be seriously harmed by deposits of dental calculus (tartar), a combination of minerals and bacteria found in the mouth. The bacterial associated with tartar can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organisms as streptocci, staphylococci, pneumococci, etc. are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Because the periodontal pockets cannot be cleaned by brushing or the use of dental floss, infection becomes progressive and constant. Due to, among other things, the effect of the mouthwash of this invention has on the microorganism causing the disease etc., in these advanced disease stages the mouthwash can cure and alleviate such advanced periodontal diseases.

Another embodiment of this invention involves the method of contacting a body cavity, the gastrointestinal canal, the urinary canel or the like with an effective amount of a liquefied composition which prevent infection from occurring and the growth of pathogenic microorganisms. The liquefied composition contains an effective amount of a non-necrotic fatty acid compound prepared from an unsubstituted, unsaturated fatty acid having at least one double bond, a liquid carrier, an effective amount of a buffering agent and an effective amount of ethanol. The pH of the liquefied composition is between 8 and 11. The disclosure on the mouthwash components, etc., applies here. The most preferred method involves the use of a liquefied composition which contains about 5 percent of sodium oleate, about 1.5 percent of ethanol, enough disodium hydrogen phosphate to adjust the pH to about 9.8 and the remainder water.

The liquefied composition can be used for its "germ fighting qualities".

The liquefied compositions of this invention can be used in any flesh incision or the like. The liquefied composition prevents (or helps) infection of the tissue incision, even after suturing or other closing off of the incision.

For surgical work, as little as 0.5 percent by weight of sodium oleate can be used, but higher percentages are preferred.

The liquid composition of this invention can be used when and after medical probing devices have been inserted into the various body cavities and tracts.

The mouthwash or liquid composition of this invention apparently renders various microorganisms, e.g., Streptococci, non-pathogenic by an electrolytic type of action. The microorganisms are prevented from becoming polarized in massive groupings—the liquid composition causes a dispersion of the microorganisms in the body fluids, which keeps them from becoming pathogenic. The mechanism may be that the liquid composition prevents or inhibits the microorganisms from producing toxins. The microorganisms are prevented from becoming morbidly pathogenic.

(The plaque forming bacteria in the mouth stick to the ridges of the teeth. It may be that the mouthwash of this invention achieves plaque formation prevention by not allowing such bacteria from seating and becoming pathogenic. The mouthwash does not open up the enamel to attack by stripping of any protective, non-plaque, non-calculus material from the face of the teeth.)

The mouthwash or liquid composition of this invention is not systemic acting. The mouthwash of this invention is not bacteriostatic or bacteracidal or antibacterial or the like, in the normal sense of such terms. The mouthwash or liquid composition apparently keeps the microorganisms (or brings about a reduction in the microorganisms population).

The composition of this invention can be used as a deodorant. It can be directly applied as a liquid, or can be placed on an absorbent pad or the like and applied in liquid form by putting on the affected surface.

Due to the effect that the mouthwash of this invention has on microorganisms, the mouthwash can be used to eliminate "bad breath", while removing and preventing bad breath. Another application involves the use in the grooming of dogs, cats, etc—for example, the unsightly plaque and tartar of show animals could be removed, as well as halitosis eliminated, by the mouthwash of this invention.

Unless otherwise stated or indicated, in the following examples and throughout this specification, all percentages, parts and proportions are expressed on a weight basis.

The following examples further illustrate, but do not limit this invention.

EXAMPLE 1

A mouthwash composition containing 5 weight percent of sodium oleate, 1.5 weight percent of ethanol, enough sodium dihydrogen phosphate to obtain a pH of 9.8 and the remainder sterile distilled water (q.s.). The mouthwash composition was placed in 16 ounce bottles. A person, known to have substantial dental plaque deposits, chewed a dental plaque disclosure tablet (which contains 2 percent erythrosin, i.e., F.D.C. Red # 3, a water soluble dye)—the person's teeth were red in those locations where there were plaque deposits (especially around the gums and in the spaces between the teeth). The person gargled with about 20 ml. of the mouthwash composition for 3 minutes. The gargling involved swirling the mouthwash in the mouth around and through the teeth. There was some foaming of the mouthwash composition in the region of the teeth during its use. Any such foaming does not mean the mouthwash is not in contact with the teeth since the mouthwash is being swirled around and between the teeth. No red dye was seen on the teeth.

The person repeated the dye mouthwash sequence twice. Each time there was much less foaming of the mouthwash composition in the region of the teeth during gargling—little or no foaming appears to be an indication that the plaque has been almost or completely removed. Then another dye tablet was chewed by the person and only a few very small regions of red were noticed on a few teeth about the gum lines between adjacent teeth. Essentially all of the substantial plaque deposits on the teeth had been removed.

(The plaque was removed by the mouthwash and it was not just a matter of the dye being leached out, etc.)

EXAMPLE 2

The person in Example 1 gargled using the mouthwash of Example 1 in the morning after breakfast and just before retiring in the evening. This was repeated for several weeks. There was no fresh build up of dental plaque deposits. At each mouthwash usage, the dye only colored relatively small portions of the teeth. The mouthwash completely removed the dyed portions (even at the gum lines between adjacent teeth). Plaque deposits were prevented on the teeth.

EXAMPLE 3

Examples 1 and 2 were repeated using a mouthwash identical to that of Example 1, except that it only contained 3 weight percent of sodium oleate and 1.2 weight percent of ethanol. The plaque deposits were removed from the teeth and the build up of any plaque deposits was prevented.

EXAMPLE 4

Examples 1 and 2 were repeated using a mouthwash identical to that of Example 1, except that it only contained 1.2 weight percent of sodium oleate and 0.7 weight percent of ethanol. The plaque deposits were removed from the teeth and the build up of any plaque deposits was prevented.

EXAMPLE 5

Examples 1 and 2 were repeated using a mouthwash composition comprised of a liquefied composition containing 5 weight percent of potassium oleate, 1.5 weight percent of ethanol, enough potassium dihydrogen phosphate to obtain a pH of 9.8 and 50 ml. of sterile distilled water (q.s.). The plaque deposits were removed from the teeth and the build up of any plaque deposits was prevented. But the results were not as good as those obtained in Examples 1 and 2.

EXAMPLE 6

Using the mouthwash composition of Example 1, a cotton swab was wetted with the mouthwash composition. The wetted cotton tip portion of the swab was rubbed over the entire surface of a person's teeth (the cotton swab being wetted as needed). After a few minutes wait, the mouth was rinsed out with water. A plaque disclosing tablet was chewed before the mouthwash treatment. The entire procedure was repeated once a day for twelve more days. The dental plaque had been removed and a total of 13 c.c. of mouthwash had been used. This illustrates how a dentist or dental assistant can remove a patient's dental plaque by repeated application of the mouthwash of this invention without having to scrap the deposit areas with a sharpened tool. (The cumulative swabbing, waiting, and rinsing time for the 13 applications was one hour and twenty minutes.)

EXAMPLE 7

The mouthwash of Example 1 was used twice a day for a person for six months. Whiteness measurements were made at the start and end of the six month period. The person's teeth were substantially whiter at the end of the six mouth period.

EXAMPLE 8

The mouthwash of Example 1 was utilized in a clinical test of rats and beagles. Administration was at extravagent dosage tests, both by topical, intra and oral application and by tests. There were 10 rats in the test formulation group and 10 rats in a placebo group. There were 4 dogs in the test formulation group plug in an placebo group. The placebo formulation was a complete formulation minus the sodium oleate. The formulation was administered daily for a period of 30 days. Observations were made daily on the animals for local tissue reactions or changes in the animals. At the end of the 30 day period a number of tissue samples were tested for histopathology evaluation.

The placebo formulation was not effective in removing plaque, whereas the composition of Example 1 was extremely effective in removing plaque. Beagles are known to be the hardest species in which to remove plaque. Th mouthwash of Example 1 was extremely effective in removing plaque from the beagles teeth. There are no adverse tissue, behavior, etc. resulting or found during the 30 day test. No diarreha occurred in the test animals.

EXAMPLE 9

The dye (or dental plaque disclosing agent) used in Example 1 dyes the plaque on the teeth. The dye has an affinity for dental or teeth plaque. The dye is not leached out by the mouthwash of Example 1. The dye is not soluble in fatty acids. The tablet did not dissolve in corn oil after 4 days and only very slowly dissolved in ethanol.

EXAMPLE 10

A person having gingivitis, serious receeding of the gums, additional loosened teeth and heavy plaque deposits, gargled twice a day with the mouthwash of Example 1. At the end of the six month period the gingivitis problem was eliminated and the gums had firmed up to such an extent that the teeth were no longer loose and had returned to their original alignment. A decrease in caries was noticed. The general state of the mouth of the person was very much healthier.

EXAMPLE 11

Examples 1 and 2 were repeated. The plaque disclosing tablets were not used. Plaque deposit levels and amounts were determined by the use of Dr. Herbert Brilliant's plaque detection light system. A dye was used which is invisible to the eye but is yellow under defracted light. The test confirmed that plaque was removed, and its formation prevented, by the mouthwash of Example 1.

EXAMPLE 12

Examples 1 and 2 were repeated except that the mouthwash also contained a small amount of an orange flavorant.

EXAMPLE 13

A Streptococcus equi culture received from ATCC in deactivated dried ampule form. The dried ampule of Streptococcus equi was activated with ½ cc sterile milk at 100° F. The Streptococcus equi was streaked via sterile swab onto two sheep blood agar plates. Plate N was streaked after addition of 5 cc. of sterile saline to the activated Streptococcus equi at the same time. Plate O was streaked after addition of 5 cc of sterile saline and 1 cc of the liquefied composition (mouthwash) of Example 1 was mixed with the activated Streptococcus equi for 2 minutes. The plates were placed in the incubator for 48 hours at 100° F. Plate N had good growth after 48 hours and plate O had no growth.

Then a swab of activated Streptococcus equi was placed in 2 cc of sterile saline for 2 minutes and than placed on sheep blood agar plate A. A swab of activated Streptococcus equi was placed in 2 cc of the liquefied composition (mouthwash) of Example 1 for 2 minutes and then placed on a sheep blood agar plate B. The plates were placed in the incubator for 48 hours at 100° F. Plate A had good growth after 48 hours and plate B had no growth.

This shows that the liquefied composition of this invention is effective against gram positive bacteria. (In this field, the liquefied composition, of Example 1 is just as effective at full strength as at a 5:1 water to liquefied composition dilution.)

EXAMPLE 14

The first test of Example 13 was repeated using Streptococcus pyogenes. The dilution factor was the same, but the microorganism was only heated at 100° F. at 24 hrs. There was no growth on the invention treated plate, but there was heavy growth on the untreated plate. It is felt that the invention composition may keep the microorganism cells from dividing.

EXAMPLE 15

The two tests of Example 13 was used against Ps. aeruginosa, Salmonella sp. 24, Salmonella sp. 21, S. agalactine, S. dysgalactiae, S. lactis, S. aureus str. 1. S. aureus str. 2, and Proteus sp. At both levels, the result was that there was a "pacification" of the various bacteria species—there was no growth or inhibition (reduction) of the species, but there was a placing of the microorganisms in a kind of limbo where they could not grow or become pathogenic.

What is claimed is:

1. The method of treating and controlling gingivitis and related periodontal diseases of the gingival tissue which comprises contacting the diseased gingival tissue with a liquefied composition comprised of a therapeutically effective amount of a non-necrotic fatty acid compound prepared from an unsubstituted, unsaturated fatty acid having at least one double bond, a liquid carrier, a buffering agent and ethanol, the pH of said liquefied composition being between 8 and 11.

2. The method as described in claim 1 wherein said fatty acid compound is a fatty acid salt prepared from an unsaturated fatty acid having one double bond and from an alkali metal or an alkali metal compound or a basic alkali metal compound.

* * * * *